(12) United States Patent
Hartman

(10) Patent No.: US 6,447,537 B1
(45) Date of Patent: Sep. 10, 2002

(54) TARGETED UV PHOTOTHERAPY APPARATUS AND METHOD

(76) Inventor: Raymond A. Hartman, 3003 Azahar St., Carlsbad, CA (US) 92009

( * ) Notice: Subject to any disclaimer, the term of this patent is extended or adjusted under 35 U.S.C. 154(b) by 67 days.

(21) Appl. No.: 09/598,272

(22) Filed: Jun. 21, 2000

(51) Int. Cl.[7] .................................................. A61N 5/06
(52) U.S. Cl. .......................... 607/94; 607/90; 250/504
(58) Field of Search ........................ 607/88–94; 606/2–3, 606/9–13, 17–19

(56) References Cited

U.S. PATENT DOCUMENTS

| | | |
|---|---|---|
| 1,800,277 A | 4/1931 | Boersler |
| 3,712,984 A | 1/1973 | Lienhard |
| 3,869,614 A | 3/1975 | Munk |
| 3,887,813 A | 6/1975 | Allington |
| 4,095,113 A | 6/1978 | Wolff |
| 4,100,415 A | 7/1978 | Blaisdell et al. |
| 4,103,175 A | 7/1978 | Levin |
| 4,155,025 A | 5/1979 | Dobrusskin et al. |
| 4,177,384 A | 12/1979 | Wolff |
| 4,272,679 A | 6/1981 | Blades |
| 4,298,005 A | 11/1981 | Mutzhas |
| 4,309,616 A | 1/1982 | Wolff |
| 4,354,139 A | 10/1982 | Konijnendikj et al. |
| 4,444,190 A * | 4/1984 | Mutzhas ........................ 607/94 |
| 4,469,951 A | 9/1984 | Coco et al. |
| 4,558,700 A | 12/1985 | Mutzhas |
| 4,703,184 A | 10/1987 | Wolff |
| 4,719,386 A | 1/1988 | Toho |
| 4,909,254 A | 3/1990 | Wilkinson |
| 4,959,551 A * | 9/1990 | Schlitt .......................... 607/94 |
| 4,967,090 A | 10/1990 | Schlitt |
| 5,146,355 A | 9/1992 | Prince et al. |
| 5,205,291 A | 4/1993 | Potter |
| 5,211,467 A | 5/1993 | Seder |
| 5,306,445 A | 4/1994 | Reed et al. |
| 5,344,433 A * | 9/1994 | Talmore ........................ 607/88 |
| 5,399,499 A | 3/1995 | Paz-Pujalt et al. |
| 5,405,368 A | 4/1995 | Eckhouse |
| 5,441,531 A | 8/1995 | Zarate et al. |
| 5,557,112 A | 9/1996 | Csoknyai |
| 5,565,685 A | 10/1996 | Czako et al. |
| 5,591,219 A | 1/1997 | Dungan |
| 5,628,744 A * | 5/1997 | Coleman et al. ............... 606/12 |
| 5,720,772 A * | 2/1998 | Eckhouse ..................... 607/88 |
| 5,731,658 A | 3/1998 | Lengyel et al. |
| 5,736,744 A | 4/1998 | Johannsen et al. |
| 5,836,999 A | 11/1998 | Eckhouse et al. |
| 5,846,684 A | 12/1998 | Paz-Pujalt et al. |
| 5,849,027 A | 12/1998 | Gart et al. |
| 5,925,034 A | 7/1999 | Buckley et al. |
| 5,955,840 A | 9/1999 | Arnold et al. |
| 6,223,071 B1 * | 4/2001 | Lundahl et al. ............... 607/91 |

FOREIGN PATENT DOCUMENTS

| | | |
|---|---|---|
| DE | 41 12275 | 11/1992 |
| DE | 198 38 304 A1 | 3/2000 |
| DE | 199 46 125 C1 | 1/2001 |
| EP | 0 592 794 A2 | 8/1992 |
| EP | 0 867 151 A2 | 9/1998 |
| GM | 76 13 630 | 11/1976 |

OTHER PUBLICATIONS

John A. Parrish, M.D. and Kurt F. Jaenicke, B.A., Action Spectrum for Phototherapy for Psoriasis, Journal of Investigative Dermatology, 1981, pp. 359–362, vol. 76, No. 5, The Williams Wilksons Co.

* cited by examiner

*Primary Examiner*—Michael Peffley
*Assistant Examiner*—Pete Vrettakos
(74) *Attorney, Agent, or Firm*—Brown, Martin, Haller & McClain, LLP

(57) ABSTRACT

A targeted UV phototherapy apparatus has a UV radiation source for emitting UV radiation at a first wavelength and a phosphor element separate from the source for converting the UV radiation in the first wavelength to a different UV wavelength in the therapeutic UVB or UVA range. A radiation directing assembly directs radiation from the UV source to the separate phosphor element, and a shaped exit aperture placed directly against a lesion directs radiation emitted from the phosphor element onto a predetermined target area of the lesion.

35 Claims, 5 Drawing Sheets

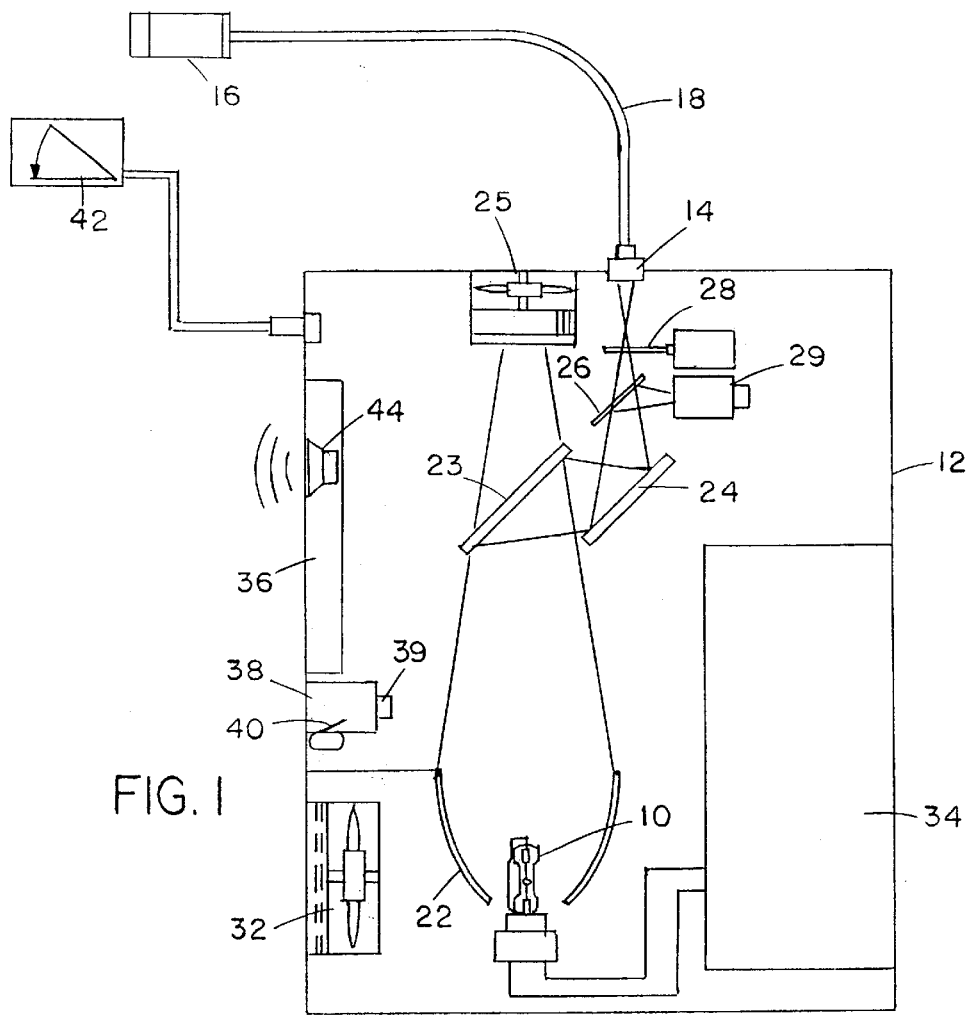
FIG. 1
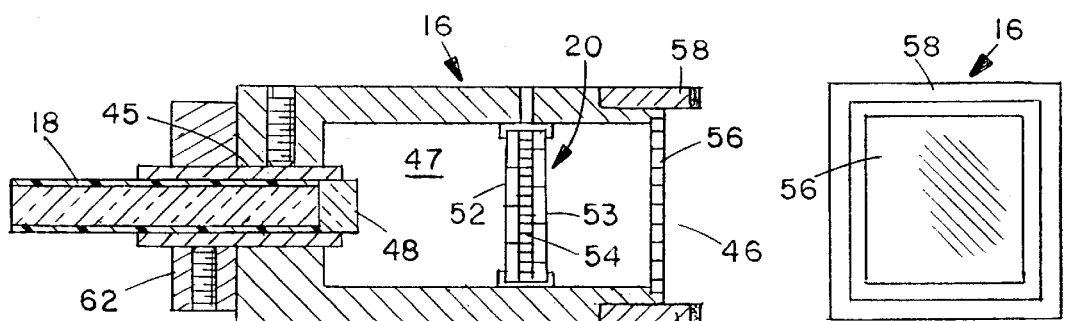
FIG. 2
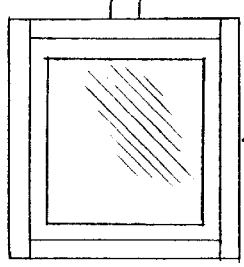
FIG. 3B
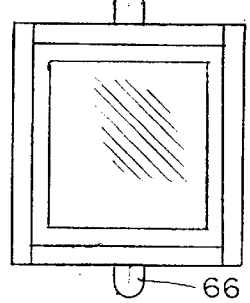
FIG. 3C
FIG. 3A

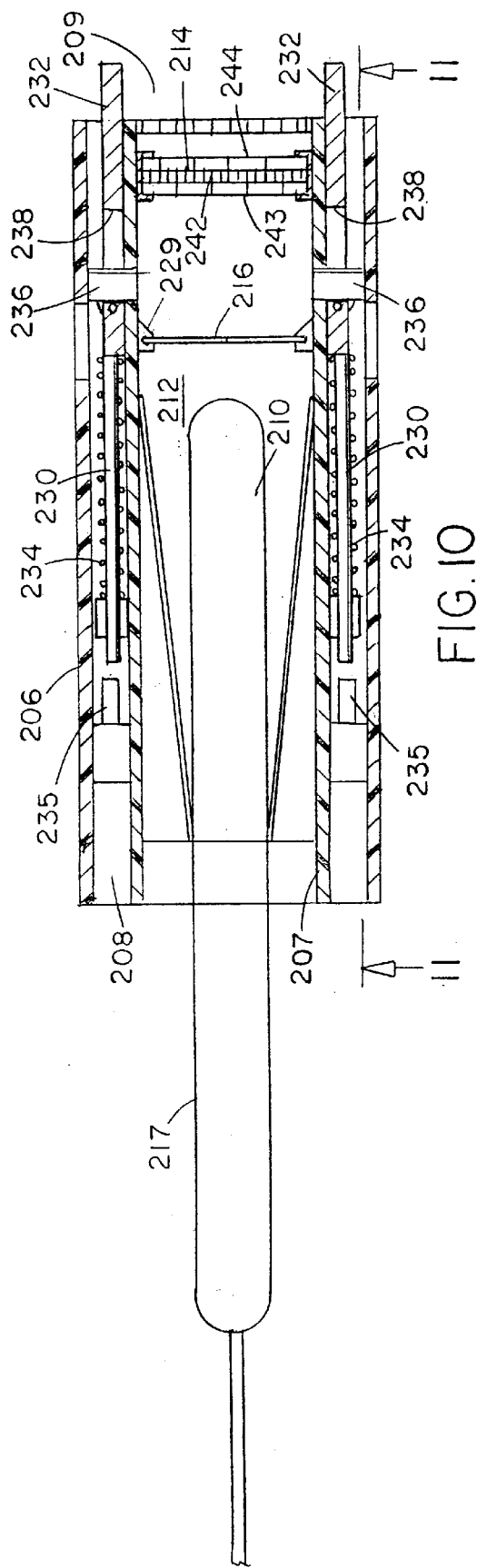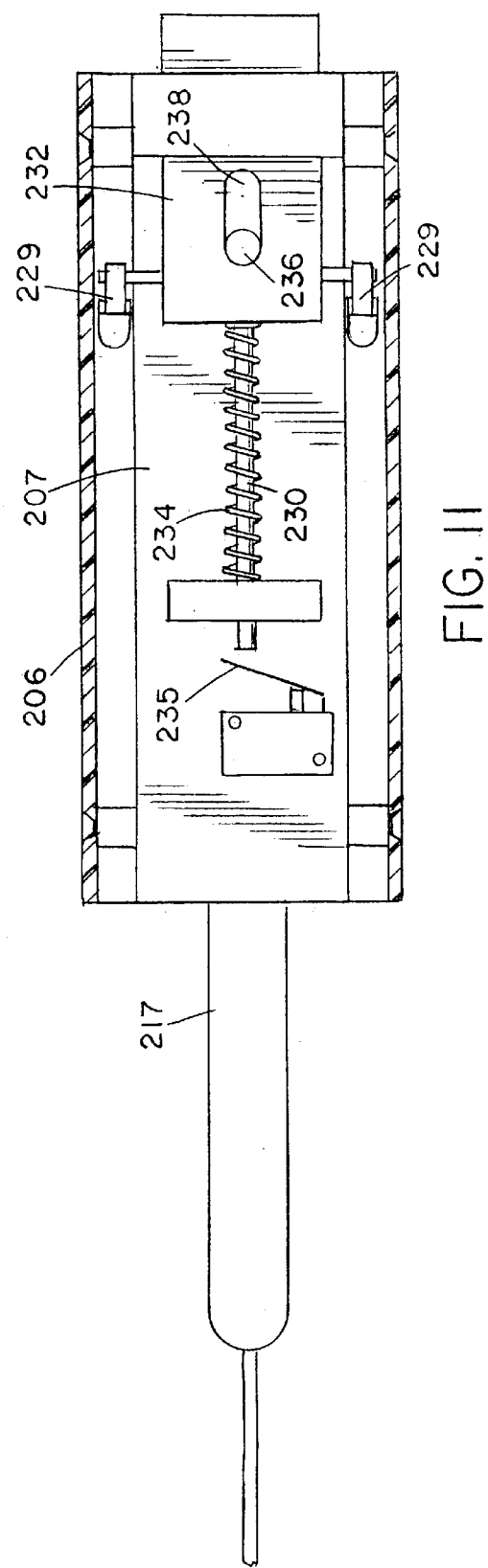

TARGETED UV PHOTOTHERAPY APPARATUS AND METHOD

BACKGROUND OF THE INVENTION

The present invention relates generally to a UV phototherapy apparatus and method for treatment of dermatoses or skin diseases such as psoriasis, vitiligo, eczema, rosacea, alopecia, and the like, and is particularly concerned with a targeted UV phototherapy apparatus and method in which radiation is applied to successive specific areas of a lesion.

Phototherapy is the use of ultraviolet radiation to achieve therapeutic benefit to dermatoses (psoriasis, vitiligo, rosacea, alopecia, eczema). The UV spectrum is divided into UVA (320–400 nm), UVB (290–320 nm) and UVC (100–290 nm). The UVA region is considered the longwave UV spectrum responsible for tanning effects, the UVB region is considered the sunburning region (erythemal region), and UVC is considered the germicidal region. Typically, both UVA and UVB radiation has been used for treatment of dermatoses. Treatment with UVA radiation is called photochemical therapy and involves the use of a photosensitizing agent, psoralen, and the administration of UVA radiation. The basis for phototherapy is believed to be the direct interaction of light of certain frequencies with tissue to cause a change in immune response. U.S. Pat. No. 5,696,081 of Ullrich describes the immune response caused by UVA and UVB radiation.

Phototherapy has a long history of treating psoriasis dating back to 1926 when natural solartreatments such as the Goekerman regimen and Heliotherapy (sunlight rich in UVB at the Dead Sea) were practiced. Heliotherapy is still practiced today. However, these natural solartreatments have mostly given way to modern booths or chambers that provide artificial UVA and/or UVB radiation. Although the benefits of UVA and UVB are known in dermatoses treatment, the adverse affects upon healthy tissue, particularly of UVB radiation, are also well known and a medical concern.

Most of the devices designed for phototherapy, both in the UVA and UVB, are table top projectors for irradiating the face or feet, or booth or chamber types of devices (solaria). Various UV booth apparatuses are revealed in U.S. Pat. Nos. 4,095,113, 4,103,175, 4,100,415, 4,703,184, 4,177,384, 4,959,551, 4,469,951 and 4,309,616. All of these devices rely upon tubular fluorescent or tubular mercury bulbs as UV sources. The booths are generally composed of multiple banks of bulbs, and irradiate large areas, usually the whole body. Large unaffected portions of the body can be protected with draping or wrapping materials, but this is impractical for most clinical use. The large area (whole body or limb) radiation pattern of these devices is a result of the emission characteristics of the light sources. The diffuse, lambertian emission patterns from these elongated, cylindrical bulbs are difficult to aim or direct to specific areas. To achieve sufficient radiation levels to provide therapeutic affect, large numbers of bulbs are required to achieve treatment times within practical limits. It is common for a booth to have 24 to 48 bulbs to achieve these practical fluence levels.

Generally, the dose of UVB radiation administered in a booth is limited by erythemal (sunburning) action. The absolute amount of UVB that a given person can tolerate before burning varies by skin type and prior exposure. It also varies with the composition of the UVB, because shorter wavelengths have greater erythemal activity. Normally, before treatment is given, the minimum erythemal dose (MED) for each patient is determined by applying different radiation doses in small patches to healthy tissue. These patches indicate the amount of energy (usually expressed in $mj/lcm^2$) that will result in sunburning the patient. It is typical for the patches to be viewed at 24 hours, and the patch that is slightly pink is considered the MED level. A single booth treatment starts at some percentage (often 70%) of this MED, and then may be increased in follow up sessions as tolerance builds up due to tanning. A typical cycle of treatments for therapeutic success in a booth is 15 to 30 treatments, usually administered in 2 to 3 treatments per week. The amount of radiation given in a given session is limited by the radiation exposure of the healthy tissue. Sunburning the entire body is not only painful, but also medically unwise.

A similar technique is used for UVA treatment, but the dose is called the MPD and the reading is generally 72 hours after exposure. In both cases, however, the MED or MPD is determined by radiation on healthy (non-lesional) tissue.

Much of the UVA therapy has been replaced by PUVA therapy, called photochemical therapy, where the photosensitizer psoralen or one of its derivatives is used with UVA radiation. PUVA treatment has proven to have long term oncological manifestations not seen with UVB treatment. However, when UVB treatment has not been successful, the alternative of PUVA does provide relief, albeit at a potential health risk.

It has been demonstrated that some lesional tissue (psoriatic plaque for example) can withstand much more UVB radiation than healthy tissue. This is largely due to the thickness of the plaque areas. However, the radiation delivered to the plaque in booth therapy is limited to the amount of radiation that the adjacent health tissue can withstand. There are three negative aspects of booth UVB treatment. First, the radiation is provided to both healthy and lesional tissue, thus increasing the total body UVB exposure. It has been demonstrated that this cumulative total body exposure has carcinogenic implications. Second, the low radiation threshold of healthy tissue limits the amount of radiation that may be delivered per session to the lesional areas. This sub-optimal dosage results in an increased number of treatments to achieve the cumulative lesional radiation required for therapeutic success. Third, the increased number of treatments that result from low plaque doses again increases the total body radiation received.

The article entitled "Action Spectrum for Phototherapy of Psoriasis", by John A. Parrish, M.D. and Kurt F. Jaenicke, B.A., published in the Journal of Investigative Dermatology, Vol. 76, No. 5, p. 359–362 (1981) describes the psoriasis action spectrum from 253 nm to 313 nm. The results in this article indicate that radiation below 296 nm is highly erythemal but not therapeutic. The article also reports that the level of radiation to deliver 1 MED at 300 nm is about $\frac{1}{10}$the radiation level required to achieve 1 MED at 313 nm. This confirms the higher erythemal activity of shorter wavelength UVB. Conventional UVB fluorescent sources provide UV radiation from 275–340 nm, a result of the fluorescent material bandwidth, and hence provide significant radiation of erythemal activity without therapeutic affect. Since a high proportion of this conventional flourescent radiation is non-therapeutic, but erythemally limiting, it necessitates a larger number of treatments.

The presence of the erythemally limiting but non-therapeutic radiation from conventional sources has led to the development of more effective UVB lamps for phototherapy. Sources of monochromatic radiation at 308 nm are available in the form of excimer lamps (U.S. Pat. No.

5,955,840). Also, tubular fluorescent lamps with nearly monochromatic output at 311 nm (U.S. Pat. No. 4,354,139) are available. Both these lamp sources suffer from the disadvantages of large area radiation, i.e. erythemal limits per treatment and healthy tissue radiation. However, many reports are available on the advantages of monochromatic UVB from these lamps. One advantage is the lack of non-therapeutic, erythemal radiation below 296 nm. This allows more of the delivered UVB radiation to be of therapeutic value before the MED is reached. Conventional UVB bulbs which operate in the broad range of 275–340 nm may provide undesirable radiation which promotes cellular proliferation.

As opposed to this large area radiation, targeted phototherapy is the application of radiation to specific areas, defined by the geometry or exit aperture of a delivery device. The radiation dose is generally, although not necessarily, constant through out the application to a lesion. The dose administered during an irradiation cycle is known, and the boundary of the irradiated area is known. It may be thought of as placing a penlight against the skin. The area is known to be the exit area of the penlight, and, in the case of targeted phototherapy, the dose may be controlled. Repeating this pattern of the penlight exit face over a lesion allows for complete coverage of the lesion.

Tubular fluorescent lamps in general cannot be effectively used for targeted radiation delivery. This is due to the difficulty in collecting the light from these elongated, diffuse sources, and focusing it onto the skin or into an optical guide. Targeted, or spot delivery of radiation in general requires that the light source be collimated or be of a small intense arc that allows efficient fiber optic coupling. Targeted UV phototherapy systems typically employ lasers and are very expensive.

Monochromatic radiation at 308 nm can be provided by xenon chloride excimer lasers, and such sources are capable of directed site delivery as a result of their coherent beams. The disadvantage of such sources is the high cost of equipment and associated maintenance. They nominally sell in the hundreds of thousands of dollars, and contain high-pressure toxic gases that must be regularly exchanged.

SUMMARY OF THE INVENTION

It is an object of the present invention to provide a new and improved targeted UV phototherapy apparatus and method.

According to one aspect of the present invention, an apparatus for directing targeted UV radiation to a predetermined area of a patient to be treated is provided, which comprises a UV radiation source for emitting UV radiation in a first wavelength, a phosphor element separate from the source for converting the UV radiation in the first wavelength to a different UV wavelength, a radiation directing assembly for directing radiation from the UV source to the separate phosphor element, and an exit aperture for directing radiation emitted from the phosphor element onto a predetermined target area of a patient.

Preferably, a handpiece is provided which has an internal chamber in which at least the phosphor element is mounted, and the exit aperture is provided at one end of the handpiece. In one embodiment of the invention, the UV radiation source is separate from the handpiece, and the radiation directing assembly comprises an optical guide connecting the UV source to an inlet end of the handpiece. In an alternative embodiment, the UV source is mounted in the handpiece itself, facing the phosphor element, and the radiation directing assembly comprises a reflector for directing radiation from the UV source onto the phosphor element.

In a preferred embodiment of the invention, the UV source comprises a source of UVC radiation, and the phosphor element is of a luminescent material for converting UVC radiation to UVB or UVA radiation. Different phosphor elements may be provided for UVB and UVA radiation, and selectively connected to the source depending on the type of UV radiation to be used for treatment. The UVC source may be a deuterium lamp, rare gas discharge lamp, mercury lamp, mercury short arc lamp, or high intensity discharge (HID) mercury halide lamp.

According to another aspect of the present invention, a method of treating lesional tissue is provided, which comprises the steps of:

directing radiation from a source of UV radiation onto a separate phosphor element;

converting the radiation received from the source into UV radiation of a predetermined different wavelength in the phosphor element; and directing the converted radiation from the phosphor element onto a predetermined area of lesional tissue through an exit aperture of predetermined shape and dimensions.

In this invention, the phosphor is removed from inside of the lamp and placed near the area to be irradiated. This retains the high conversion efficiency and wavelength selection flexibility of phosphors, without the short lifetime problems of placing such phosphors in a mercury plasma environment. By moving the phosphor outside the lamp and placing it close to the area to be treated, targeted UV radiation is possible, and the lifetime of the phosphor is also significantly increased. This technique also enables the output efficiency of the phosphor to be improved by increasing the energy density of the exciting radiation. The term phosphor as used herein refers to an inorganic material capable of being excited by a source of radiation and emitting a second radiation of longer wavelength.

This invention is a considerable improvement over traditional whole body irradiation in phototherapy booths using fluorescent lamps. In a tubular fluorescent lamp, a phosphor material is coated on the inside of the tube and a baking process is used to drive out organic binders used to make the coating adhere to the tube. This can cause some oxidation of the phosphor, making it less efficient. The phosphor and lamp lifetime is also affected by the inherent design characteristics of fluorescent tubes. Output decay is caused by absorption of mercury by the phosphor, and considerably reduces phosphor lifetime. A typical useful lifetime for fluorescent lamps used in phototherapy booths is only 500 to 2000 hours, and 24 or more lamps are typically used in such booths. Thus, lamp replacement is a significant expense. Additionally, light collection and concentration from such lamps is very difficult, so an individual to be treated can be exposed for only a short time interval to avoid damage to healthy skin, or must be draped to cover healthy skin areas.

In contrast, the present invention provides targeted radiation directed only onto a lesional area of the skin, using only one UV lamp, and significantly increases the effective phosphor lifetime, as well as the output efficiency.

BRIEF DESCRIPTION OF THE DRAWINGS

The present invention will be better understood from the following detailed description of some exemplary embodiments of the invention, taken in conjunction with the accompanying drawings in which like reference numerals refer to like parts and in which:

FIG. 1 is a schematic cross-sectional view of a targeted UV phototherapy apparatus according to a first embodiment of the present invention;

FIG. 2 is an enlarged cross-sectional view of the handpiece of the apparatus of FIG. 1;

FIG. 3A is an end view of the exit aperture of the handpiece of FIG. 2;

FIG. 3B is an end view similar to FIG. 3A illustrating a different keyed handpiece;

FIG. 3C is an end view similar to FIGS. 3A and 3B illustrating another keyed handpiece;

FIG. 10 is a view of the handpiece similar to that of FIG. 9 but with the shutter closed; and FIG. 11 is a cross-section on the lines 11—11 of FIG. 10 illustrating the control and switch arrangement for controlling shutter opening and closing.

DETAILED DESCRIPTION OF THE DRAWINGS

Figure 4:
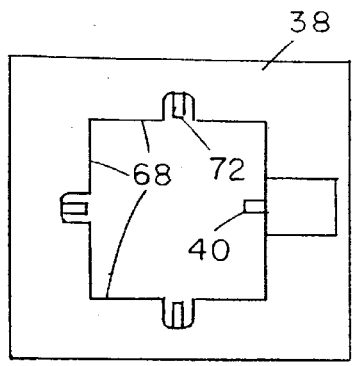
FIG. 4 is an end view of the calibration port of the apparatus of FIG. 1.

FIG. 1 illustrates a targeted UV phototherapy apparatus according to a first exemplary embodiment of the invention. The apparatus basically comprises a UV lamp source 10 mounted in an outer housing 12 having a UV output port 14, and a handpiece 16 for directing UV radiation to a predetermined area of a lesion to be treated connected to the UV output port 14 via an optical guide 18. An optical assembly within the housing 12 directs radiation from the source 10 to the output port 14. Handpiece 16 contains a phosphor element 20 for converting the UV radiation received from the source 10 to a different wavelength radiation suitable for therapeutic purposes.

UV source 10 preferably comprises a high UVC producing lamp. There are a wide variety of high UVC producing, inexpensive lamp sources, such as deuterium lamps, mercury lamps, mercury short arc or mercury halide HID lamps. In the exemplary embodiment illustrated in FIG. 1, lamp 10 comprises a short arc (1.5 mm. to 8 mm.) mercury or doped mercury lamp. The lamp is preferably a 200 watt lamp and is made of a material which prevents ozone formation caused by 185 nm. radiation. Suitable short arc MSR lamps are available from Phillips and other manufacturers. Such lamps are inexpensive, easy to install, and have lifetimes above 2000 hours.

The optical assembly for directing radiation from the lamp or source 10 to output port 14 includes a symmetrical elliptical reflector 22 enclosing the lamp, and a series of two UVC reflective mirrors 23,24 for directing radiation towards port 14. A beam splitter 26 and a shutter 28 are located in the path of reflected radiation from the second mirror 24 to outlet port 14. The elliptical reflector 22 may be made of metal or a dichroic coated glass which is UV reflective. The elliptical reflector 22 collects and directs radiation onto the first UVC mirror 23, which is arranged at an angle of 45 degrees to the radiation path. This mirror reflects 95% to 99% of the UVC radiation while transmitting any radiation outside the UVC range to a heat sink 30. UVC light is then reflected from the second UVC mirror 24 to the outlet port via beam splitter 26 and shutter 28. Beam splitter 26 has an output linked to energy sensor 29 for continuous monitoring of the lamp UVC output. Although a single UVC mirror would provide adequate UVC spectral isolation, particularly if used with a UV bandpass filter, the use of a plurality of UVC mirrors reduces unwanted radiation at a nominal cost.

Short arc UV lamps have the advantage of providing a good UVC output with a low 185 nm radiation content, and also allow for efficient collection of around 50% to 60% of the emitted radiation with a symmetrical reflector in the arrangement illustrated in FIG. 1. Preferably, a fan 32 is mounted in the housing for directing cooling air onto the elliptical reflector to avoid heat distortion.

The lamp 10 is connected to a suitable power supply and ignition module 34 within the housing 12. If the lamp 10 is an AC arc lamp, module 34 comprises a ballast and ignitor. If the lamp 10 is a DC arc lamp, module 34 will comprise a DC supply and ignitor. A control unit 36 for monitoring and controlling lamp operation is also mounted in housing 12, along with a calibration port 38 for handpiece 16. An energy sensor 39 is mounted at the inner end of calibration port 38. At least one mechanical switch 40 is mounted on a side wall of port 38 for detecting insertion of the end of the handpiece into the port 38. A manually operable switch, such as a foot pedal switch 42, is provided for switching the apparatus on and off. A control panel (not illustrated) will be provided on the outer wall of the housing to display various system parameters such as the sensor outputs. An audible alarm device 44 may also be provided in the control unit. This will be arranged to emit an alarm signal if the energy sensor 29 does not detect any radiation after the lamp is turned on, for example. In this situation, the shutter 28 is also controlled to close, and the audible alarm will alert the operator to a potential problem. The control unit is preferably designed to allow self-diagnostics concerning the transmission characteristics of the optical guide and handpiece.

As described above, the UVC output at output port 14 is connected via optical guide 18 to the input of handpiece 16. The optical guide 18 may be a UVC liquid light guide, a fused silica fiberoptic guide, or a fiberoptic bundle. A liquid UVC light guide provides an inexpensive conduit, and the input surfaces can be quite large, affording easy and direct coupling to the reflector output. The light guide numerical aperture is selected to match the output geometry of the focusing mechanism in housing 12. Coupling a beam to a light guide from a lens or elliptical reflector is well known to those in the field. The input acceptance angle of the light guide must equal or exceed the focusing angle of the reflector for maximum coupling.

An exemplary embodiment of the handpiece 16 is illustrated in more detail in FIG. 2 and 3a. The handpiece 16 basically comprises a tube of square or rectangular cross-section having an inlet opening 45 at one end, an exit aperture 46 at the opposite end, and an internal bore or chamber 47. The outlet end 48 of light guide 18 extends into the chamber 47 through inlet opening 45. A phosphor cell 20 is secured in chamber 47 between the outlet end of the optical guide 18 and the exit aperture 46 of the handpiece. In this embodiment, phosphor cell 20 comprises a pair of plates 52,53 with a phosphor layer 54 sandwiched between the plates. The plate 52 facing the outlet end of light guide 18 must be transmissive to UVC but can be reflective of UVB so that all UVB radiation created by the phosphor layer will be reflected back towards the exit aperture. The plate 53 facing the exit aperture is blocking or reflective to UVC radiation, but transparent to other UV radiation. This prevents UVC radiation from escaping from the phosphor cell and irradiating the patient, and also redirects any UVC radiation back into the phosphor layer for increased excitation.

In one example, the first plate 52 which faces the light guide outlet end 48 is of a clear fused silica material, and is coated on the phosphor side with a UVB reflective coating. The phosphor layer is of a material which converts UVC radiation to UVB radiation. For example, layer 54 may be a gadolinium doped matrix which converts UVC to nearly monochromatic 311 nm. radiation. Such a matrix may include yttria, borates, silicates or ternary aluminates activated by cations from the group consisting of Bi, Pb, Sr, or Ca. Alternatively, the phosphor may be an alkali halide matrix doped with Ag or TI. Another suitable UVB phosphor is $(Ca,Zn)_3(PO4)_2$:TI which has an emission peak at 310 nm.

The second plate 53 enclosing phosphor layer 54 may be of any material which blocks or reflects UVC while transmitting other UV wavelengths, such as an optical filter or a dichroic mirror. In one example, where the phosphor layer is of $(Ca,Zn)_3(PO4)_2$:TI, the plate 53 is an optical filter of WG305 which shapes or tunes the output to be largely within 300 to 330 nm. as well as blocking any UVC radiation. In other embodiments, the plates 52,53 may be of clear fused silica, sapphire, or other optical glasses.

By enclosing the phosphor layer within two plates, the phosphor is kept free from dust and moisture. The phosphor cell is sealed and held together in a frame, using a suitable sealant which is UV resistant, such as epoxy or silicone rubber. The sealing is done in an inert, dry atmosphere to eliminate water and oxygen which can react with the phosphor, and the sealing also prevents human exposure to the phosphor, which may contain potentially harmful elements.

The body of the handpiece must be of a material which is opaque to UV radiation to prevent escape of any radiation from the handpiece, other than via the exit aperture. Suitable materials for the handpiece are aluminum or various plastics such as polycarbonate, as well as UV blocking glass materials. In one example, the handpiece is of a material which is transmissive in the visible region, to allow the skin area to be seen during treatment. The inside walls of chamber 47 are polished so as to reflect scattered radiation on each side of the phosphor cell 20. The exit aperture 46 is covered by an exit plate 56 which may be a bandpass or other filter, or a dichroic mirror to further refine the spectral characteristics. The plate 56 is sealed to the handpiece to keep the chamber 47 free of dust and moisture.

In the illustrated embodiment, a disposable slide-on tip 58 is secured to the exit end of the handpiece so as to project outwardly from the exit aperture, as best illustrated in FIG. 2. The tip 58 surrounds the periphery of the exit aperture, and is of a clear, UV blocking plastic material. The tip 58 may have an ink or dye containing felt or porous pad 60 secured at its outer end. This allows an area of skin which has been irradiated to be marked. In use, the handpiece will be held with the exit aperture facing the skin region to be treated and the marking pad 60 touching the skin. This ensures that the same area is not treated twice.

The handpiece 16 is of square cross-section with polished, reflective inner walls and a square output aperture. This allows the circular cross-section beam exiting the light guide to be converted into a square beam exiting aperture 46. The UVC beam exiting from light guide 18 will have a natural divergence according to the numerical aperture of the light guide. This will spread the beam, and the beam will be reflected and re-reflected from the polished walls of chamber 47 to provide an output of generally square cross-section. The UV blocking tip 58 allows visualization of the lesion area while blocking UV radiation from exiting into the room.

In the exemplary embodiment illustrated in FIG. 2, the handpiece 16 is releasably coupled to the light guide 18 via a releasable coupling 62, and different handpieces may be provided which contain different phosphor cells for producing different UV outputs. For example, as illustrated in FIGS. 3a, 3b, and 3c, three different handpieces 16, 16a, and 16b may be provided for selective connection to light guide 18, depending on the type of therapeutic radiation which the physician wishes to use. For example, handpiece 16 may contain a phosphor cell having a phosphor layer of a material for producing nearly monochromatic 311 nm UVB radiation, such as a layer of a gadolinium doped matrix. Handpiece 16a may contain a phosphor cell with a phosphor layer for producing UVB radiation in the range from 300 to 320 nm., such as $(Ca,Zn)_3(PO4)_2$:TI. The third handpiece 16b may contain a phosphor cell having a phosphor layer of a material for producing UVA radiation, such as $SrB_4O_7F$:Eu, which has a peak at 360 nm., $YPO_4$:Ce, which has a peak at 357 nm., or $BaSi_2O_5$:Pb, which has a peak at 350 nm.

As illustrated, the three different handpieces are preferably keyed to readily enable each one to be distinguished from the other two, using a calibration port 38 as illustrated in FIG. 4. The first handpiece 16 has no external projections, while the second handpiece 16a has a single projecting rib or key 64 projecting from one of its side faces, and the third handpiece 16b has two projecting ribs or keys 64,66 projecting from opposite side faces. Calibration port 38 is of square cross section and dimensions substantially matching those of the handpieces, with three of the side walls 68 of the port having indents or grooves 70 for receiving any projecting keys 64,66 on a handpiece inserted into the port. A mechanical switch 72 is mounted in each of the grooves 70, in addition to the mechanical switch 40 which projects from the non-indented side wall into the port to detect the presence of a handpiece. The outputs of all of the switches are connected to the control unit 36, which will determine which particular handpiece has been inserted based on which of the switches are activated. Thus, for example, if only switch 40 is activated, the handpiece inserted must be the first handpiece 16 which has no projecting keys to activate any of the other switches 72. A display device on the control unit will be controlled to indicated that the handpiece is the 311 UVB handpiece.

In an alternative embodiment, a phosphor cell may be provided which contains mixtures of different phosphors to give differing output characteristics. For example, different mixtures of a gadolinium doped matrix and $(Ca,Zn)_3(PO4)_2$:TI with a WG305 filter will give an output of 90% in the 300–320 nm range with different proportions of short wave (300 to 310 nm) and longer wave (310 to 320 nm) radiation. For thicker plaques, a physician may want to use a higher proportion of longer wavelength radiation, and for clearing plaques, a higher proportion of shorter wavelength radiation may be desired. Such alternatives are readily available with this invention, simply by changing the phosphor or phosphor mixture. A large number of different handpieces containing phosphor cells with different output wavelengths may be provided, allowing the physician a great amount of flexibility in selecting the optimum treatment wavelength or combination of wavelengths. Additionally, several phosphor cells may be used together in the same handpiece, with the phosphor in the first cell producing an excitation wavelength for the next cell. This expansion of the flexibility of phosphor technology to meet various wavelength criteria in a targeted fashion is not only applicable to phototherapy, but also to photo dynamic therapy.

The operator can calibrate a handpiece by depressing foot switch 40, or a switch on the handpiece itself. Calibration curves that compensate for detector wavelength sensitivity can then be applied to the calibration. The radiation emitted from the handpiece is measured by the energy sensor 39 at the inner end of the calibration port. Software diagnostics in control unit 36 measure the stability of the output, and comparison with the output of sensor 29 will allow self-diagnostics concerning the transmission characteristics of the optical guide and handpiece. If the energy sensor 29 does not receive any radiation after the lamp 10 is switched on, the shutter 28 will close and the operator will be alerted to a potential problem. Shutter sensors (not illustrated) will be provided and connected to control unit 36 to indicate the shutter position.

In the embodiment illustrated in FIG. 1, the UVC source or lamp is a short arc mercury or doped mercury lamp 10, and radiation is reflected in a light path from the lamp to dichroic mirror 23 by means of an elliptical reflector 22. Dichroic mirror 23 reflects UVC radiation to the second dichroic mirror 24, but transmits higher wavelength radiation. The transmitted radiation from mirror 23 is absorbed by black body heat sink and fan unit 25. The majority of the UVC radiation reflected from the second mirror is transmitted by beam splitter 26 and directed to output port 14, with around 5% of the radiation being directed to the power sensor 29.

Figure 6:
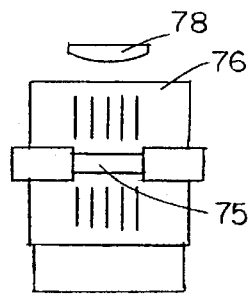
FIG. 6 is a section on the lines 6—6 of FIG. 5.
Figure 5:
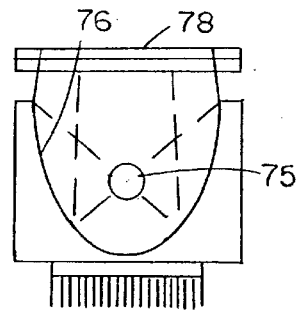
FIG. 5 is a cross-sectional view of an alternative UV source for the apparatus of FIG. 1.

FIGS. 5 and 6 illustrate an alternative UVC lamp 75 and associated optics for replacing lamp 10 and elliptical reflector 22. In this alternative, the UVC source is a tubular arc lamp with a 1–2 inch arc, such as a medium arc mercury or doped mercury lamp. A cylindrical elliptical reflector 76 is placed behind lamp 75, with lamp 75 at the first focal point of reflector 76. Reflector 76 then produces a line of reflected light at the second focal point of reflector 76. A cylindrical lens 78 is used to convert this line to a point. The lens 78 and reflector 76 have different focal points, and the offset of the lens from the reflector makes the two focal points coincide near the input 14 to the optical guide 18. Other parts of the optical assembly, such as the dichroic mirrors and bandpass filter, will be identical to the assembly of FIG. 1. The optics used are fused silica to ensure transmission of the UVC radiation. A parabolic mirror with two cylindrical lenses will accomplish the same effect.

In the embodiment of FIG. 2, the handpiece 16 contains a phosphor cell comprising a phosphor layer sandwiched between two plates. FIGS. 7A to 7E illustrate some alternative handpieces with different phosphor arrangements. The handpieces of FIGS. 7A to 7E are otherwise identical to that of FIG. 2, and like reference numerals have been used for like parts as appropriate.

Figure 7A:
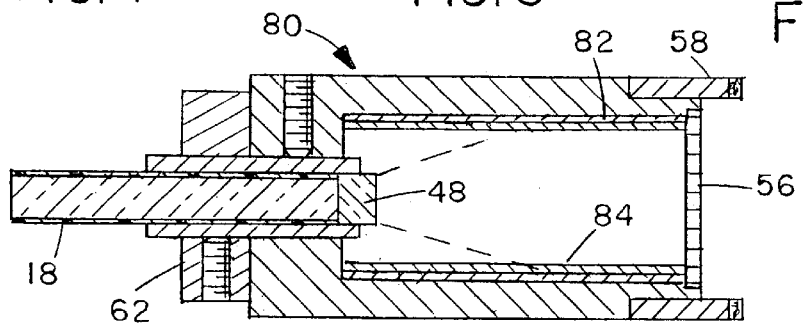
FIGS. 7A to 7E illustrate some alternative handpieces with different phosphor cell arrangements for use in the apparatus of FIG. 1.

In the handpiece 80 of FIG. 7A, the phosphor cell 20 of FIG. 2 is replaced with a phosphor layer 82 lining the inner surface of the handpiece and an inner quartz sleeve or binder 84 holding the phosphor layer in place and sealing it. The phosphor is illuminated by the diverging beam emitted from the exit end 48 of the light guide 18, as indicated in FIG. 7A, as well as by internal reflections. The light exit end is sealed with a filter 56 which passes either UVA or UVB radiation but not UVC radiation. In this version, the entire handpiece forms the phosphor cell, unlike FIG. 2 where a separate phosphor cell 20 is mounted in the handpiece.

Figure 7B:
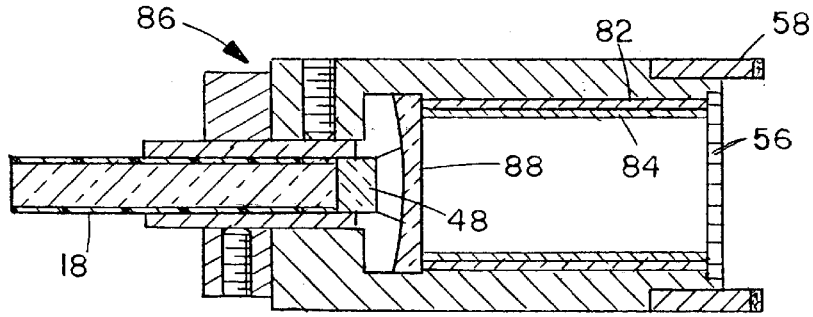

FIG. 7B illustrates a modified handpiece 86 which has a phosphor lining similar to the handpiece of FIG. 7A, and like reference numerals have been used as appropriate. However, in this embodiment, a plano-convex lens 88 is placed over the exit end 48 of the light guide 18 so as to increase the exit angles of the UVC radiation exiting the light guide.

Figure 7C:
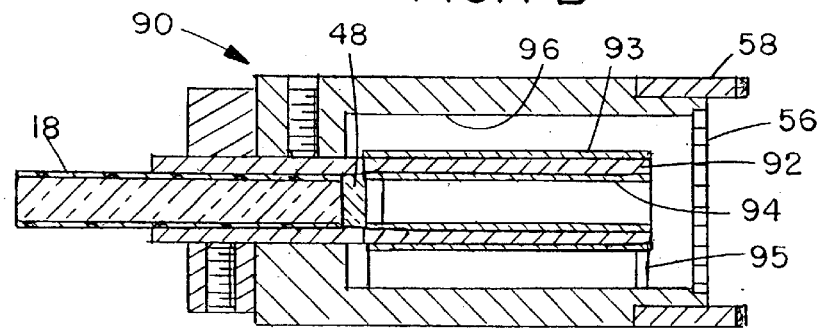

Another alternative handpiece 90 is illustrated in FIG. 7C. In this alternative, a cylindrical phosphor layer 92 is trapped between two concentric tubes 93,94 extending from the exit end 48 of the light guide. A support 95 is provided at the free end of the tubes 93,94. The inner surface 96 of the handpiece is polished to provide reflections until the UVB or UVA radiation exits the handpiece.

Figure 7D:
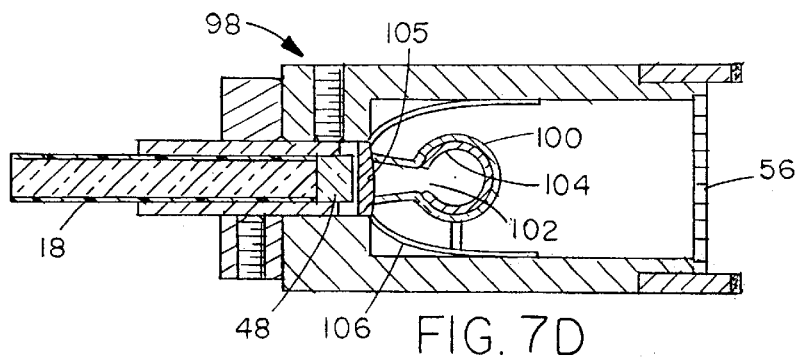

FIG. 7D illustrates another alternative handpiece 98 in which a hollow sphere or bulb 100 of quartz or the like has an inlet opening 102 attached to the outlet end 48 of the light guide. A phosphor coating 104 is provided on the inner surface of sphere 100, although the coating may alternatively be provided on the outer surface of the sphere. A miniature quartz plano convex lens 105 covers the outlet end 48 of the light guide. The output of the light guide is focused onto and into the quartz sphere containing the phosphor, and radiated outward. A reflective mirror 106 may be mounted behind sphere 100 to redirect radiation to the outlet of the handpiece.

Figure 7E:
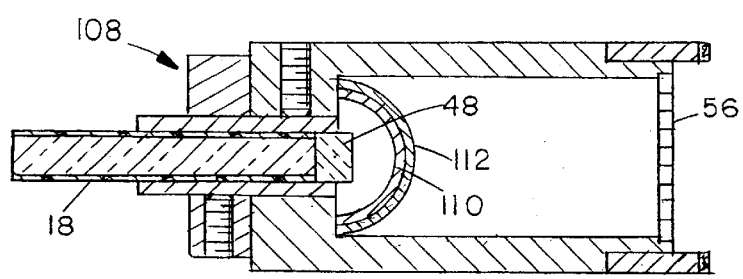

FIG. 7E illustrates a handpiece 108 with a hemispherical or half-cylindrical quartz mount 110 with a phosphor layer 112 painted or coated on the outer surface of the mount, facing the exit plate or face plate 56. This provides an increased area of phosphor over the phosphor disc of FIG. 2, which increases the phosphor amount exposed to radiation. The inside of the handpiece is polished to maximize internal reflections until the UVA or UVB emitted by the phosphor exits the handpiece.

Figure 8:
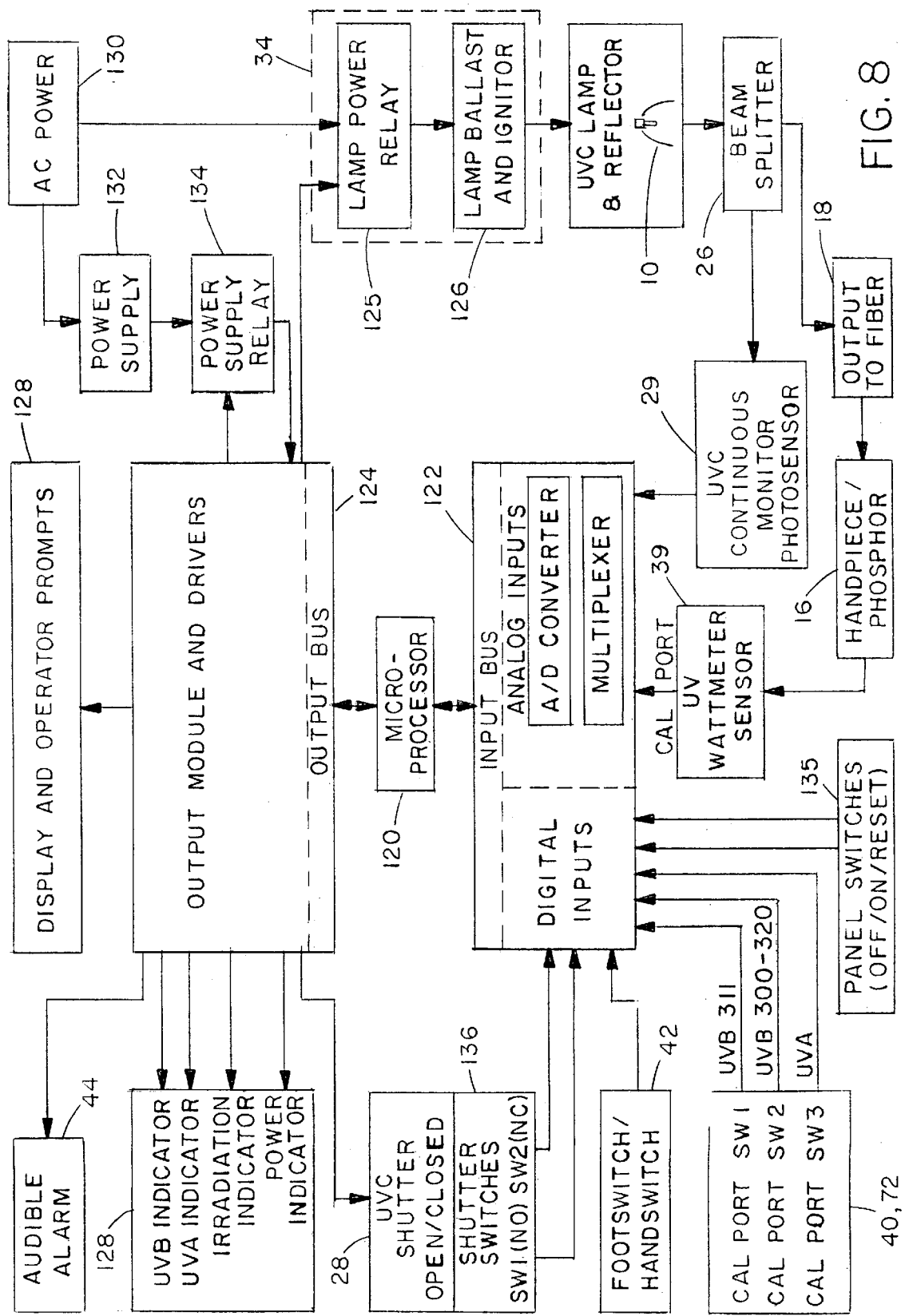
FIG. 8 is a block diagram of the control system for the apparatus of FIG. 1.

FIG. 8 is a block diagram illustrating one possible embodiment of a control system for the apparatus of FIG. 1, incorporating the control unit 36 and power supply and ignition unit 34. The control system basically comprises a microprocessor 120 in control unit 36 which is programmed to monitor inputs from the various sensors and input switches via an input bus 122, and to provide control outputs to an output module 124 which has drivers for controlling operation of the shutter 28, lamp power supply via relay 125 and ballast and igniter 126, and the various indicators on the display unit 128. An AC power supply 130 is connected to a power supply 132 and relay 134 for the output module and drivers, and to the input of the lamp power relay 125. The control panel preferably also has switches 135 for switching the apparatus on or off, and for reset of the control unit.

The microprocessor 120 is programmed to control timing of the open/closed state of the shutter 28 by actuating the shutter switches 136. The operator may vary the irradiation cycle by suitable input at the control panel 128. The microprocessor also monitors the energy sensor 39 of the calibration port 38 to detect the power output of a handpiece inserted in the port, and the switches 40 and 72 to determine which particular handpiece has been inserted. Indicators on the control panel will be actuated to light up in response to insertion of the respective handpieces so that the operator can ensure that the correct handpiece has been secured to the lightguide. Alternatively, rather than the mechanical key arrangement illustrated in FIGS. 3A to 3C and 4, the calibration port may have sensors for detecting the type of radiation emitted by the handpiece as well as the power level.

The output of photosensor 29 at the beamsplitter is also connected to microprocessor 120. The beamsplitter reflects around 5% of the energy to the sensor 29 to enable the lamp output to be continuously monitored. If this sensor does not receive any radiation after the lamp has been switched on, the shutter 28 is closed and an audible and/or visual alarm will be actuated to alert the operator to a potential problem. The audible and/or visual indicators are also arranged to provide an indication of the status of the irradiation cycle.

The phototherapy apparatus of FIGS. 1 to 8 is very efficient and easy to use. The focusing mechanism in housing 12 allows efficient coupling of the UVC radiation output of a selected lamp into the light guide 18, By using a series of two dichroic reflectors which reflect UVC and transmit other wavelengths, a high percentage of the UVC radiation can be collected while eliminating unwanted wavelengths. The handpiece 16 incorporates a phosphor for wavelength conversion to a selected UVB or UVA radiation, and provides a means for targeting the radiation onto a selected skin area, avoiding irradiation of adjacent, healthy areas. This invention retains the high conversion efficiency and wavelength selection flexibility of phosphors, without the problems of reduced phosphor lifetime when the phosphor is placed in a mercury plasma environment.

The square output aperture defines the area of applied radiation, and allows for convenient movement to adjacent areas without overlap, unlike a circular or other aperture without straight edges. The felt tip of the handpiece may be provided with absorbent ink or dye marking pads, or provision for attaching marking pens, so that the user can see which areas of a lesion have been irradiated. Alternatively, a UV sensitive dye may be applied to the lesion, and the dye will change in appearance when radiation has been applied to an area. Adjacent areas of skin may be protected by an overcoat of zinc oxide or a UV absorbing oil painted on prior to a phototherapy procedure. Alternatively, a thin shim material that is UV opaque may be placed under the edge of the exit aperture to mask healthy tissue along the lesion edges. The material of the tubular handpiece is preferably transparent so that the practitioner can see the area under irradiation, allowing for accurate mask placement.

Figure 9:
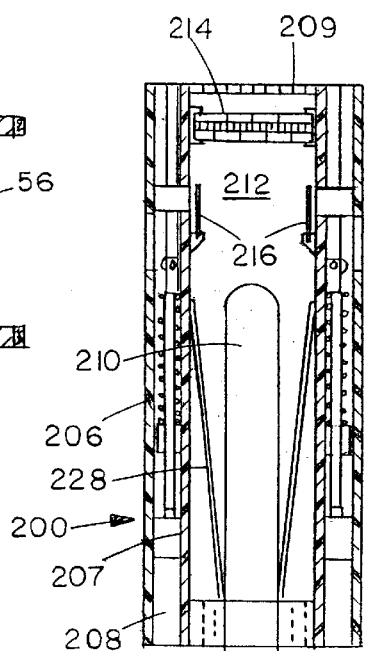
FIG. 9 is a cross-sectional view of a targeted UV phototherapy apparatus according to another embodiment of the invention.
Figure 9:
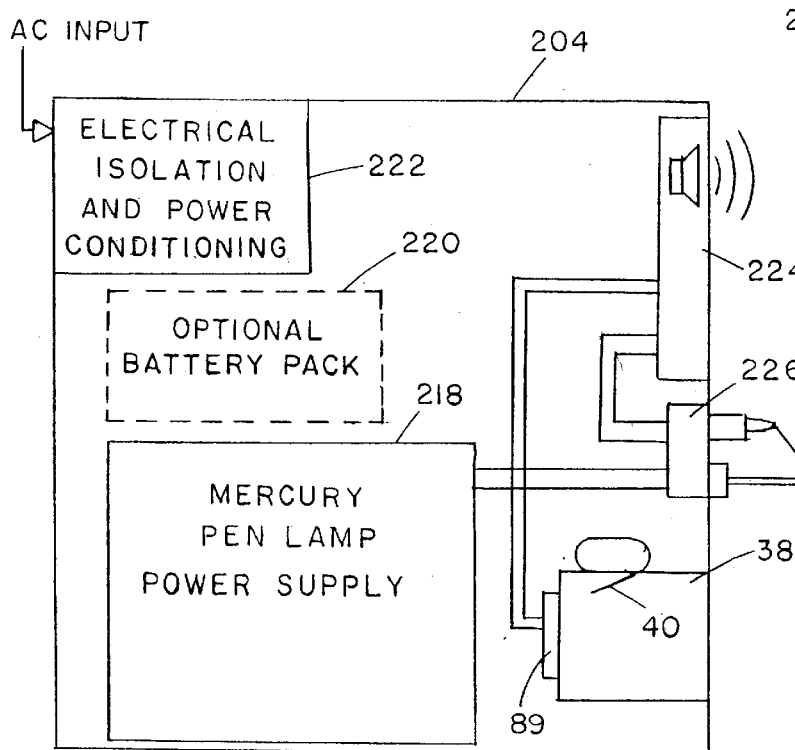

FIGS. 9 to 11 illustrate a UV phototherapy apparatus according to another embodiment of the invention, in which the UV lamp is located in a handpiece rather than in a separate housing as in FIG. 1. In this embodiment, a handpiece 200 for applying UV radiation directly to a targeted area of a lesion is connected via an electrical cable 202 to a base unit 204 containing the electronics and power conditioning for the system.

Handpiece 200 basically comprises a tubular outer housing 206 of generally square or rectangular cross-section, and an inner body or tube 207 of corresponding cross-section mounted concentric with outer housing 206 to leave a gap 208 between the inner and outer housing. Inner tube 207 has a generally square exit aperture 209 at one end. A UVC source such as a low or medium pressure mercury lamp 210 is mounted in a chamber 212 in the housing 207 facing the exit aperture. Such lamps are available commercially and are commonly known as pen lamps, pencil lamps, or capillary double bore lamps. A phosphor cell 214 is mounted in chamber 212 between the lamp 210 and the exit aperture for converting UVC radiation emitted by lamp 210 into UVB or UVA radiation of the desired wavelength or wavelength range. The radiation from the lamp 210 is collected and directed towards the exit aperture by a conical reflector 228. A shutter assembly 216 is mounted between the lamp and the exit aperture for preventing radiation from exiting the handpiece unless it is properly engaged with a lesion to be treated. A handle 217 is provided in the exemplary embodiment for easy gripping and application of the exit aperture against the skin.

The base unit 204 contains a power supply 218 for the mercury pen lamp, an optional battery pack 220, and an electrical isolation unit and trickle charger 222 for the battery pack. A control unit 224 for the system is also provided in the base unit 204, and this will include a display, control panel, audible and visible alarm, and control switches similar to the control system of the previous embodiment, as illustrated in detail in FIG. 8. A connection port 226 is provided for connecting the power supply to the lamp, and also for receiving shutter status information from the handpiece, as described in more detail below. The base unit is also provided with a calibration port 38 with associated sensors which is similar or identical to that of the previous embodiment, and like reference numerals have been used for like parts as appropriate.

The shutter assembly 216 in the handpiece will now be described in more detail. FIG. 10 illustrates the two hinged shutter members in a closed position blocking UV radiation from exiting the handpiece, while FIG. 9 illustrates the shutter members in an open position. Each shutter member is pivotally linked via linkage mechanism 229 to a respective sliding actuator pin 230 which is slidably mounted on one side of the inner tube 207 between the inner tube and outer housing 206. A pressure pad or plate 232 extends from the end of each pin out of the forward end of the handpiece. Each pin 230 and attached pressure pad 232 is biased into the fully extended position of FIGS. 10 and 11, in which the shutter is open, by a spring 234. A switch 235 is located behind the inner end of each pin so as to be closed, or actuated, when the pin is moved into the inner position of FIG. 9, in which the shutter is closed. The outputs of the switches 235 are connected to the base control unit 224 via cable 202. Movement of each pressure pad and pin is guided in a linear path by means of guide posts 236 projecting from opposite sides of the inner tube and extending through respective slots 238 in the pressure pads or plates, as best illustrated in FIG. 11.

The arrangement is such that, when the pressure pads 232 are placed against the irradiation target, they will both slide back into the handpiece, opening the shutters via linkage mechanism 229, allowing radiation to exit the handpiece. When the handpiece is removed from the skin, the springs 234 force the pads back into the extended position, closing the shutters and opening the switches 235. The shutters may alternatively be activated by means of solenoids mounted in the handpiece and controlled by control unit 224.

The outer housing 206 of the handpiece is preferably of plastic material and serves to isolate the unit both electrically and thermally. The handpiece is sealed against dust and moisture by a UVC blocking glass or filter over the exit aperture 209. The end plate may also act as a diffuser or wavelength tuning element to eliminate unwanted radiation for various phosphors. The pen lamp 210 may be a low wattage lamp in the range of 5–10 watts with an efficient UVC production, with 90% of the radiation emitted being at 254 nm. If additional cooling is necessary, a heat sink may be connected to the handpiece and cover the handle portion 240 of the lamp.

In the illustrated embodiment, the phosphor cell 214 comprises a phosphor layer 242 sandwiched between first and second plates 243,244. As in the embodiment of FIG. 2, the first plate 243, which faces the lamp, transmits UVC but may be reflective of UVB or UVA, so that all UVB or UVA radiation created by the phosphor layer is reflected back towards the exit aperture. The second plate 244, which faces the exit aperture, blocks UVC radiation but is transmissive to UVB or UVA radiation, depending on which type of radiation the handpiece is designed to emit. Examples of suitable materials for the end plates 243,244 are given above in connection with the phosphor cell of FIG. 2.

If a 10 watt lamp is used in the handpiece of FIGS. 9 to 11, it will produce about 2.5 watts of UVC at 254 nm., which is directed by the conical reflector towards the phosphor cell. With a 50% system loss and 40% conversion efficiency of UVC to UVB (normal for UV phosphors), about 0.5 watts of UVB or UVA is produced. Although this is a lower output than would be desirable for clinical purposes, it provides an effective and safe level for home use.

The output of the handpiece may be increased, if desired, by the use of small medium pressure mercury bulbs of the H38/43/45/46 type. Such sources are available in 40 to 100 watts in tubes less than one inch in length and 0.5" diameter. These tubes are commonly found in commercial mercury bulbs which place a second glass envelope around the tube to eliminate the UVC radiation. This envelope can be removed to allow the tubes to be used as the UVC source in this apparatus. Another good UVC source which may be used in the handpiece is a grid lamp, which has a "spaghetti" type of tubing bent into grids which are often rectangular. This type of lamp may be built into a cylindrical or conical shape to accommodate the shape of the handpiece, and has a very high UVC output with low thermal production.

The phosphor cell may be of different design to that of FIGS. 9 to 11, as in the previous embodiment, and specifically may take any of the alternative forms illustrated in FIGS. 7A to 7E. It may also comprise a sleeve which fits over the lamp or a coating over the reflector.

In operation, the operator first selects the energy dose using switches on the control panel. The handpiece can be calibrated by placing it in calibration port 38 and pushing it forwards to open the shutters. The detector 39 determines when the output is stable and performs the energy output calibration, which may be provided to the operator by means of an output display on the control panel. After calibration is complete, the irradiation cycle is initiated by placing the handpiece on a targeted skin area and pushing it flush to the skin. This action forces the pressure pads 232 backwards into the handpiece, activating the switches 235 and opening the shutters 216. The duration of the irradiation cycle is determined by the calibration data and the selected energy dosage. In normal sub-erythemal use a cycle will typically be from two to five seconds. When the irradiation cycle is complete, an audible tone is emitted from the control unit and the user removes the handpiece from the skin. This action simultaneously closes the shutters, and the microprocessor monitors the signals from the switches to ensure that the shutters have been closed. If the shutters are not closed within a preset limit, e.g. 25% dosage above the selected dose, the power to the lamp is automatically shut off.

The operator then moves the handpiece to the next region of skin to be irradiated, repeating the process until the entire treatment area has been covered. Similar marking techniques to those described above in connection with the first embodiment may also be used in this version of the invention.

The phototherapy apparatus of the above embodiments provides a convenient means for targeted UV phototherapy, reducing the risk of irradiation of healthy skin, with the exit aperture precisely defining the area of applied radiation. The second embodiment, in which a small and inexpensive low pressure mercury bulb is contained in the handpiece, avoids the need for an optical guide, since the bulb directly energizes the UVA or UVB emitting phosphor within the handpiece. This version can be operated from an electrical wall outlet or powered by a battery, making it convenient for home use. This embodiment also eliminates the losses inherent in the reflectors, optical coupling, and optical guide. The apparatus may be programmed for a specific number of treatments by physician prescription, and the prescription can be renewed by a code provided by the physician.

This invention embodies a completely different approach to phototherapy using traditional fluorescent lighting, by completely removing the phosphor from inside the lamp and placing it near to the area to be irradiated. This retains the high conversion efficiency and wavelength selection flexibility of phosphors, without the lifetime problems associated with putting the phosphor in a mercury plasma environment. This technique also allows the output of the phosphor to be increased by increasing the energy density of the exciting or incident radiation, and the output can easily be targeted to specific areas of skin without affecting adjacent areas.

The handpiece also provides a stable, maneuverable means for radiation delivery. The handpiece is designed for radiation conversion, shaping and filtering with a defined, square or rectangular exit aperture for easier coverage of a skin area, and with provision for marking so that the operator can readily determine which skin areas have already been treated. The exit end of the handpiece is flat, so that it can be placed flush against the skin, and its borders will block emission of stray radiation into the room or surrounding skin areas. The contact portion of the handpiece may be disposable or sterilizable to reduce the risk of possible contamination from patient to patient.

The precise duration of an irradiation cycle is determined by the microprocessor based on the calibration data and the dose selection made by the practitioner.

Although some exemplary embodiments of the invention have been described above by way of example only, it will be understood by those skilled in the field that modifications may be made to the disclosed embodiments without departing from the scope of the invention, which is defined by the appended claims.

I claim:

1. An apparatus for directing targeted UV radiation to a predetermined area of a patient to be treated, comprising:
    a UV radiation source for emitting UV radiation at a first wavelength;
    a phosphor element completely separate and spaced apart from the source for converting the UV radiation in the first wavelength to a different UV wavelength;
    a radiation directing assembly for directing radiation from the UV source to the separate phosphor element; and
    an exit aperture for directing radiation emitted from the phosphor element onto a predetermined target area of a patient.

2. The apparatus as claimed in claim 1, including a handpiece having an internal chamber, the handpiece having opposite first and second ends, the exit aperture being provided at the second end of the handpiece and at least the phosphor element being mounted in the chamber.

3. An apparatus for directing targeted UV radiation to a predetermined area of a patient to be treated, comprising:
- a UV radiation source for emitting UV radiation at a first wavelength;
- a phosphor element separate from the source for converting the UV radiation in the first wavelength to a different UV wavelength;
- a radiation directing assembly for directing radiation from the UV source to the separate phosphor element;
- an exit aperture for directing radiation emitted from the phosphor element onto a predetermined target area of a patient;
- a plurality of different handpieces each having an internal chamber, each handpiece having opposite first and second ends, the exit aperture being provided at the second end of the handpiece and at least the phosphor element being mounted in the chamber; and
- each handpiece containing a different phosphor element for converting UV radiation into radiation in a plurality of different UVA and UVB wavelengths.

4. The apparatus as claimed in claim 1, comprising a base unit and a separate handpiece connected to the base unit, the handpiece having an inlet end and an exit end containing the exit aperture, the base unit including a controller for controlling operation of the apparatus.

5. An apparatus for directing targeted UV radiation to a predetermined area of a patient to be treated, comprising:
- a UV radiation source for emitting UV radiation at a first wavelength;
- a phosphor element separate from the source for converting the UV radiation in the first wavelength to a different UV wavelength;
- a radiation directing assembly for directing radiation from the UV source to the separate phosphor element;
- an exit aperture for directing radiation emitted from the phosphor element onto a predetermined target area of a patient;
- the apparatus comprising a base unit and a separate handpiece connected to the base unit, the handpiece having an inlet end and an exit end containing the exit aperture, the base unit including a controller for controlling operation of the apparatus; and
- the UV radiation source comprising a UVC lamp mounted in the base unit, and the radiation directing assembly comprising an optical guide connecting the UV source to the inlet end of the handpiece.

6. The apparatus as claimed in claim 5, wherein the base unit has an output port, the optical guide having a first end connected to the output port and a second end connected to the inlet end of the handpiece, and the base unit includes an optical focusing assembly for focusing UVC radiation from the lamp into the optical guide.

7. The apparatus as claimed in claim 6, wherein the focusing assembly includes a parabolic reflector mounted behind the lamp.

8. An apparatus for directing targeted UV radiation to a predetermined area of a patient to be treated, comprising:
- a UV radiation source for emitting UV radiation at a first wavelength;
- a phosphor element separate from the source for converting the UV radiation in the first wavelength to a different UV wavelength;
- a radiation directing assembly for directing radiation from the UV source to the separate phosphor element;
- an exit aperture for directing radiation emitted from the phosphor element onto a predetermined target area of a patient;
- a base unit and a separate handpiece connected to the base unit, the handpiece having an inlet end and an exit end containing the exit aperture, the base unit including a controller for controlling operation of the apparatus;
- the UV radiation source comprising a UVC lamp mounted in the base unit, and the radiation directing assembly comprising an optical guide connecting the UV source to the inlet end of the handpiece;
- the base unit having an output port, the optical guide having a first end connected to the output port and a second end connected to the inlet end of the handpiece, and the base unit includes an optical focusing assembly for focusing UVC radiation from the lamp into the optical guide; and
- at least one UVC reflecting dichroic mirror in the light path from the lamp to the outlet port.

9. The apparatus as claimed in claim 6, wherein the UVC lamp is selected from the group consisting of a deuterium lamp, a mercury lamp, a mercury short arc lamp, a rare gas discharge lamp, and a mercury HID halide lamp.

10. apparatus for directing targeted UV radiation to a predetermined area of a patient to be treated, comprising:
- a UV radiation source for emitting UV radiation at a first wavelength;
- a phosphor element separate from the source for converting the UV radiation in the first wavelength to a different UV wavelength;
- a radiation directing assembly for directing radiation from the UV source to the separate phosphor element;
- an exit aperture for directing radiation emitted from the phosphor element onto a predetermined target area of a patient;
- the apparatus comprising a base unit and a separate handpiece connected to the base unit, the handpiece having an inlet end and an exit end containing the exit aperture, the base unit including a controller for controlling operation of the apparatus;
- the UV radiation source comprising a UVC lamp mounted in the base unit, and the radiation directing assembly comprising an optical guide connecting the UV source to the inlet end of the handpiece; and
- the optical guide is selected from the group consisting of a UVC transmitting liquid light guide, a fused silica fiberoptic, and a fiberoptic bundle.

11. An apparatus for directing targeted UV radiation to a predetermined area of a patient to be treated, comprising:
- a UV radiation source for emitting UV radiation at a first wavelength;
- a phosphor element separate from the source for converting the UV radiation in the first wavelength to a different UV wavelength;
- a radiation directing assembly for directing radiation from the UV source to the separate phosphor element;
- an exit aperture for directing radiation emitted from the phosphor element onto a predetermined target area of a patient;
- the apparatus comprising a base unit and a separate handpiece connected to the base unit, the handpiece having an inlet end and an exit end containing the exit aperture, the base unit including a controller for controlling operation of the apparatus; and the base unit having a calibration port for releasably receiving the handpiece, the calibration port having a sensor at its inner end for detecting radiation emitted from the exit aperture, the sensor output being connected to the controller.

12. The apparatus as claimed in claim 11, including a plurality of different handpieces for selective connection to the base unit, each handpiece having a different phosphor element for converting UV radiation emitted by the source into a selected UV wavelength in the UVA and UVB range, the respective handpieces having predetermined key configurations and the calibration port having key sensors for distinguishing between the different key configurations to determine which handpiece has been inserted in the port, the key sensors having outputs connected to the controller.

13. The apparatus as claimed in claim 12, wherein there are at least three different handpieces, one handpiece having a phosphor element for emitting substantially monochromatic UVC radiation of about 311 nm, another handpiece having a phosphor element for emitting radiation in the wavelength range from 300 to 320 nm., and another handpiece having a phosphor element for emitting radiation in the UVA wavelength range.

14. The apparatus as claimed in claim 13, wherein one of the handpieces has no key projections, another handpiece has one key projection, and another handpiece has two key projections, and the calibration port has side walls, the key sensors comprising switches mounted in the side walls for detecting the key projections and producing a switch output corresponding to which of the three handpieces has been inserted in the port.

15. The apparatus as claimed in claim 1, including a shutter between the UV source and the exit aperture, and a control device for controlling opening and closing of the shutter.

16. The apparatus as claimed in claim 15, wherein the control device comprises a switch.

17. An apparatus for directing targeted UV radiation to a predetermined area of a patient to be treated, comprising:
  a UV radiation source for emitting UV radiation at a first wavelength;
  a phosphor element separate from the source for converting the UV radiation in the first wavelength to a different UV wavelength;
  a radiation directing assembly for directing radiation from the UV source to the separate phosphor element; and
  a rectangular exit aperture for directing radiation emitted from the phosphor element onto a predetermined target area of a patient.

18. An apparatus for directing targeted UV radiation to a predetermined area of a patient to be treated, comprising:
  a UV radiation source for emitting UV radiation at a first wavelength;
  a phosphor element separate from the source for converting the UV radiation in the first wavelength to a different UV wavelength;
  a radiation directing assembly for directing radiation from the UV source to the separate phosphor element;
  a rectangular exit aperture for directing radiation emitted from the phosphor element onto a predetermined target area of a patient; and
  the exit aperture comprising a square of area in the range from 1 square centimeter to 40 square centimeters.

19. An apparatus for directing targeted UV radiation to a predetermined area of a patient to be treated, comprising:
  a UV radiation source for emitting UV radiation at a first wavelength;
  a phosphor element separate from the source for converting the UV radiation in the first wavelength to a different UV wavelength;
  a radiation directing assembly for directing radiation from the UV source to the separate phosphor element;
  an exit aperture for directing radiation emitted from the phosphor element onto a predetermined target area of a patient; and
  a marking device attached to the exit aperture for marking an irradiated area.

20. The apparatus as claimed in claim 4, wherein the UV source is mounted in the handpiece facing the phosphor element.

21. The apparatus as claimed in claim 20, wherein the radiation directing assembly comprises a reflector for directing radiation from the UV source onto the phosphor element.

22. The apparatus as claimed in claim 20, including a shutter assembly mounted between the UV source and the exit aperture, and an actuator for moving the shutter assembly between the open and closed positions.

23. The apparatus as claimed in claim 22, wherein the actuator comprises at least one actuator member slidably mounted in the handpiece for movement between an extended position in which it projects out of the second end of the handpiece, and a retracted position within the handpiece, biasing means for biasing the actuator member towards the extended position, and a pivotal linkage between the shutter assembly and slidable actuator member for moving the shutter between the closed position and the open position as the actuator member moves from the extended position to the retracted position, whereby the shutter assembly is opened when a user places the extended actuator member against an area of skin to be irradiated and presses the handpiece downwardly towards the skin.

24. The apparatus as claimed in claim 1, wherein the phosphor element is a matrix containing gadolinium selected from the group consisting off yittria, borates, silicates, and ternary aluminates activated by cations from the group Bi, Pb, Sr, and Ca.

25. The apparatus as claimed in claim 1, wherein the phosphor element is an alkali halide matrix doped with Ag.

26. The apparatus as claimed in claim 1, wherein the phosphor element is selected from the group consisting of $SrB_4O_7F:E4$, $YPO_4:Ce$, and $BaSi_2O_5:Pb$.

27. An apparatus for directing targeted UV radiation to a predetermined area of a patient to be treated, comprising:
  a UV radiation source for emitting UV radiation at a first wavelength;
  a phosphor element separate from the source for converting the UV radiation in the first wavelength to a different UV wavelength;
  a radiation directing assembly for directing radiation from the UV source to the separate phosphor element;
  an exit aperture for directing radiation emitted from the phosphor element onto a predetermined target area of a patient;
  the apparatus comprising a base unit and a separate handpiece connected to the base unit, the handpiece having an inlet end and an exit end containing the exit aperture, the base unit including a controller for controlling operation of the apparatus; and
  a phosphor cell in the handpiece, the phosphor cell comprising first and second end plates and the phosphor element being sandwiched between said end plates.

28. The apparatus as claimed in claim 27, wherein the first end plate facing the first end of the handpiece is of a material which transmits UVC radiation.

29. The apparatus as claimed in claim 28, wherein the second end plate facing the exit aperture is of a material which blocks UVC radiation and transmits UVB radiation.

30. A method of treating lesional tissue, comprising the steps of:

directing radiation from a source of UV radiation onto a phosphor element which is completely separate and spaced from the UV radiation source;

converting the radiation received from the source into UV radiation of a predetermined different wavelength in the phosphor element; and directing the converted radiation from the phosphor element directly onto a predetermined area of lesional tissue through an exit aperture of predetermined shape and dimensions.

31. The method as claimed in claim 30, wherein the radiation source is a source of UVC radiation.

32. The method as claimed in claim 31, wherein the step of converting the radiation comprises converting the UVC radiation to UVB radiation in the phosphor element.

33. The method as claimed in claim 31, wherein the step of converting the radiation comprises converting the UVC radiation to UVA radiation in the phosphor element.

34. A method of treating lesional tissue, comprising the steps of:

mounting a UV source in a base unit and mounting a phosphor element in a handpiece separate from the base unit, an exit aperture being provided at an exit end of the handpiece;

directing radiation from a source of UV radiation into one end of a light guide;

connecting the opposite end of the light guide to an inlet end of the handpiece so that the UV radiation is directed along the light guide and into the handpiece;

converting the radiation received from the source into UV radiation of a predetermined different wavelength in the phosphor element; and directing the converted radiation from the phosphor element directly onto a predetermined area of lesional tissue through an exit aperture of predetermined shape and dimensions.

35. The method as claimed in claim 30, including the steps of providing the exit aperture at an exit end of a handpiece, mounting the UV source in the opposite, inlet end of the handpiece, mounting the phosphor element between the UV source and the exit aperture, and directing radiation from the UV source to the phosphor element.

\* \* \* \* \*